United States Patent
Fu

(10) Patent No.: US 10,400,004 B2
(45) Date of Patent: Sep. 3, 2019

(54) CHEMICAL SYNTHESIS METHOD OF PHILLYRIN

(71) Applicant: Li Fu, Dalian (CN)

(72) Inventor: Li Fu, Dalian (CN)

( * ) Notice: Subject to any disclaimer, the term of this patent is extended or adjusted under 35 U.S.C. 154(b) by 209 days.

(21) Appl. No.: 15/502,085

(22) PCT Filed: Dec. 23, 2014

(86) PCT No.: PCT/CN2014/094656
§ 371 (c)(1),
(2) Date: Feb. 6, 2017

(87) PCT Pub. No.: WO2016/019682
PCT Pub. Date: Feb. 11, 2016

(65) Prior Publication Data
US 2017/0233425 A1 Aug. 17, 2017

(30) Foreign Application Priority Data
Aug. 7, 2014 (CN) .......................... 2014 1 0386621

(51) Int. Cl.
*C07H 15/26* (2006.01)
*C07H 1/00* (2006.01)

(52) U.S. Cl.
CPC ............... *C07H 15/26* (2013.01); *C07H 1/00* (2013.01)

(58) Field of Classification Search
CPC .................................. C07H 15/26; C07H 1/00
USPC ....................................................... 536/18.5
See application file for complete search history.

(56) References Cited

U.S. PATENT DOCUMENTS

| 6,323,339 B1 * | 11/2001 | Seeberger ................ C07H 5/06 506/19 |
| 2010/0168054 A1 * | 7/2010 | Moutel .................... C07H 5/04 514/53 |

OTHER PUBLICATIONS

Fan, Hongyu et al, Liaoning Chemical Industry, Mar. 31, 2014, vol. 43, issue 3, pp. 241-243, English Translation.*
Li Xiaodong et al, J. Shenyang Pharmaceutical University, 2011, 28(9), 707-711; English Translation.*
Fan, Hongyu et al., "Synthesis and Structure Characterization of Phillyrin", Liaoning Chemical Industry, vol. 43, No. 3, Mar. 31, 2014, pp. 241-243.
Li, Xiaodonga et al., Highly Effective Preparative Method of Glycosylation Reagents-Glycosyl Trichloracetimidates, Journal of Shenyang Pharmaceutical, vol. 28, No. 9, Sep. 30, 2011, pp. 707-711.

* cited by examiner

*Primary Examiner* — Ganapathy Krishnan
(74) *Attorney, Agent, or Firm* — Greer, Burns & Crain, Ltd.

(57) ABSTRACT

The present invention relates to a chemical synthesis method for phillyrin. The method of the present invention comprises: first dissolving a glycosyl receptor phillygenin and a glycosyl donor in an organic solvent for glycosylation to obtain tetraacyl phillyrin; then dissolving the tetraacyl phillyrin in a second organic solvent, and adding sodium methoxide for deacylation, adding an acidic pH regulator to regulate the pH value of the reaction mixture to neutral; and finally carrying out purification treatment to obtain phillyrin. The advantages and practical values of the chemical synthesis method for phillyrin of the present invention lie in: the raw material is easy to get, the catalysts used for glycosylation are cheap and easy to get, the production cost is greatly reduced, and it can be used for industrial production.

6 Claims, No Drawings

CHEMICAL SYNTHESIS METHOD OF PHILLYRIN

This application is the U.S. National phase application corresponding to PCT/CN2014/094656 which was assigned an international filing date of Dec. 23, 2014 and associated with publication WO 2016/019682 A1 and which claims priority to Chinese Application 201410386621.8 filed on Aug. 7, 2014, the disclosures of which are expressly incorporated herein.

TECHNICAL FIELD

The invention belongs to the field of pharmacological chemistry and in particular relates to a chemical synthesis method for phillyrin.

The advantages and practical values of the chemical synthesis method for phillyrin lie in: the raw material is easy to get, the catalysts for glycosylation are cheap and easy to get, the production cost is greatly reduced, and it can be used for industrial production.

BACKGROUND ART

Fructus Forsythiae is dried fruits of *Forsythia suspensa* (Thunb.) Vahl (Oleaceae), which is mainly grown in Henan, Shanxi, Shanxi, Shandong provinces and other places in China, as well as Hubei, Hebei, Sichuan and Gansu provinces. Forsythiae is commonly used for treating diseases of acute wind-heat common cold, carbuncle and sore, tuberculous lymphadenitis, urinary tract infection, etc. A main ingredient of Fructus *forsythia* (*forsythia*) is phillyrin with antiviral, antibacterial, antioxidant, free radicals removing, antitumor and other pharmacologic effects. At present, numerous researches on extraction of phillyrin from natural *forsythia* have been reported, medicinal plant resources become increasingly scarce, and effective ingredient content is relatively low, thus chemical synthesis of phillyrin can greatly reduce cost, improve yield and play a role in protection of plant resources.

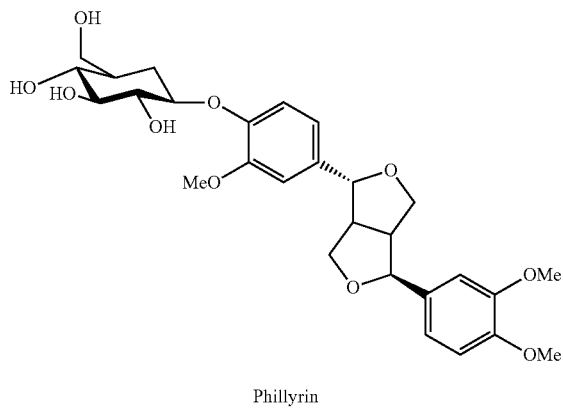

Phillyrin

Chemical synthesis of phillyrin has been researched, in 2014, Fan Hongyu et al. utilized 1-Bromo-tetra-o-acetyl-alpha-D-glucose and phillygenin for carrying out glycosylation catalyzed by a phase transfer catalyst and base and utilized sodium methoxide for deprotection to generate phillyrin [Fan Hongyu, Fu Li, Synthesis and Structure Characterization of Phillyrin, Liaoning Chemical Industry, 2014, 43, 241-243], however, synthesis yield of the method is relatively low, penta-acetyl-beta-D-glucose and 33% hydrobromic acid of acetic acid solution are required to be brominated to obtain 1-Bromo-tetra-o-acetyl-alpha-D-glucose, and hydrobromic acid does not facilitate operation for its corrosion.

SUMMARY OF THE INVENTION

The invention provides a synthesis method for phillyrin, aiming at solving the technical problems in an existing chemical synthesis process of phillyrin. The method of the invention can overcome the defects of the prior art with the high yield of a synthesized product phillyrin. The method of the invention has simple operation and technological process, short production period, high content of phillyrin in the synthesized product, high yield and obviously reduced production cost of phillyrin, and is applicable to batch preparation and industrial production.

For the purposes of the invention, in one aspect the invention provides a chemical synthesis method for phillyrin, comprising the following steps:

1) dissolving a glycosyl receptor phillygenin and a glycosyl donor in the first organic solvent, and carrying out glycosylation to obtain tetraacyl phillyrin;

2) dissolving the tetraacyl phillyrin in the second organic solvent, then adding sodium methoxide for deacylation, adding an acidic pH regulator to regulate pH value of a reaction mixture to neutral, and carrying out purification treatment to obtain phillyrin.

wherein temperature of the glycosylation in the step 1) is 0-20° C., preferably 0-10° C., and further preferably 0° C.; The reaction time of the glycosylation in the step 1) is 4-15 h, preferably 8-10 h, and further preferably 10 h.

In particular, 2,3,4,6-tetra-O-acyl-D-glucopyranosyl trichloroacetimidate is used as the glycosyl donor; dichloromethane, trichloromethane, 1,2-dichloroethane or toluene, preferably dichloromethane, is used as the first organic solvent.

More particular, 2,3,4,6-tetra-O-acetyl-D-glucopyranosyl trichloroacetimidate or 2,3,4,6-tetra-O-benzoyl-D-glucopyranosyl trichloroacetimidate is used as the 2,3,4,6-tetra-O-acyl-D-glucopyranosyl trichloroacetimidate.

Wherein the molar ratio of the 2,3,4,6-tetra-O-acyl-D-glucopyranosyl trichloroacetimidate to phillygenin is 1.0-5.0:1.

In particular, during the glycosylation of the invention, usage amount of the glycosyl donor 2,3,4,6-tetra-O-acyl-D-glucopyranosyl trichloroacetimidate is small, the yield of a glycosylation product is low, byproducts will be increased while the usage amount is increased, and the molar ratio of the glycosyl donor 2,3,4,6-tetra-O-acyl-D-glucopyranosyl trichloroacetimidate to phillygenin is preferably 1.5-2.5:1.

In particular, after the glycosyl receptor phillygenin and the glycosyl donor are dissolved in the organic solvent for glycosylation in the presence of a catalyst.

Wherein Lewis acid is used as the catalyst.

In particular, one or more of C3-C9 haloacetamides, C2-C8 silyl fluorohydrocarbyl sulfonate, C1-C6 silver fluorohydrocarbyl sulfonate and boron trifluoride etherate, preferably N-iodosuccinimide, silver trifluoromethanesulfonate, trimethylsilyl triflate or boron trifluoride etherate, and further preferably silver trifluoromethanesulfonate, trimethylsilyl triflate and boron trifluoride etherate, are used as the Lewis acid catalysts.

Wherein the molar ratio of the Lewis acid catalyst to the glycosyl donor 2,3,4,6-tetra-O-acyl-D-glucopyranosyl trichloroacetimidate is 1:1.0-10.0.

Low usage amount of the Lewis acid catalyst leads to decomposition of the glycosyl donor 2,3,4,6-tetra-O-acyl-D-glucopyranosyl trichloroacetimidate, and reduced yield; high usage amount of the Lewis acid catalyst leads to decomposition of a glycosyl donor, tetraacyl phillyrin, and reduced yield.

In particular, the molar ratio of the Lewis acid catalyst to the glycosyl donor 2,3,4,6-tetra-O-acyl-D-glucopyranosyl trichloroacetimidate is preferably 1:5.0-10.0, further preferably 1:5-6, and still further preferably 1:5.

In particular, after the glycosyl receptor phillygenin and the glycosyl donor are dissolved in the organic solvent for glycosylation under protection of inert gas and in the presence of the catalyst.

Wherein the inert protective gas is nitrogen, argon or helium, preferably nitrogen.

In particular, after the glycosyl receptor phillygenin and the glycosyl donor are dissolved in the organic solvent for glycosylation under protection of inert gas and in the presence of the catalyst and a molecular sieve.

Wherein an aluminosilicate molecular sieve or aluminosilicate powder is used as the molecular sieve.

In particular, a 3 Å-5 Å type aluminosilicate molecular sieve, preferably a 4 Å type aluminosilicate molecular sieve is used as the aluminosilicate molecular sieve.

More particular, the usage amount of the molecular sieve meets the requirement that a mass ratio of the molecular sieve to phillygenin is 1-10:1, preferably 2:1.

In particular, the method also comprises a step 1A) of quenching the glycosylation by a quenching agent before tetraacyl phillyrin is dissolved in the second organic solvent.

Wherein trimethylamine, triethylamine or sodium thiosulfate is used as the quenching agent.

In particular, the usage amount of the quenching agent meets the requirement that the molar ratio of the quenching agent to the Lewis acid is 1:1-3, preferably 1:1-1.5, and further preferably 1:1.

Wherein a mixed solution of dichloromethane and methanol is used as the second organic solvent in step 2).

In particular, the volume ratio of dichloromethane to methanol in the mixed solution of dichloromethane and methanol is 1:1-10, preferably 1:2.

Wherein the molar ratio of sodium methoxide to 2,3,4,6-tetra-O-acyl-D-gluco pyranosyl trichloroacetimidate is 1:300-500, preferably 1:375-500.

In particular, the time of deacylation is 4-12 h, preferably 4 h.

In particular, acetic acid, propionic acid or hydrochloric acid, preferably acetic acid, is used as the acidic pH adjuster.

More particular, the pH value of the reaction mixture is adjusted to 6-7.

The chemical reaction formula of the chemical synthesis of phillyrin in the invention is as follows:

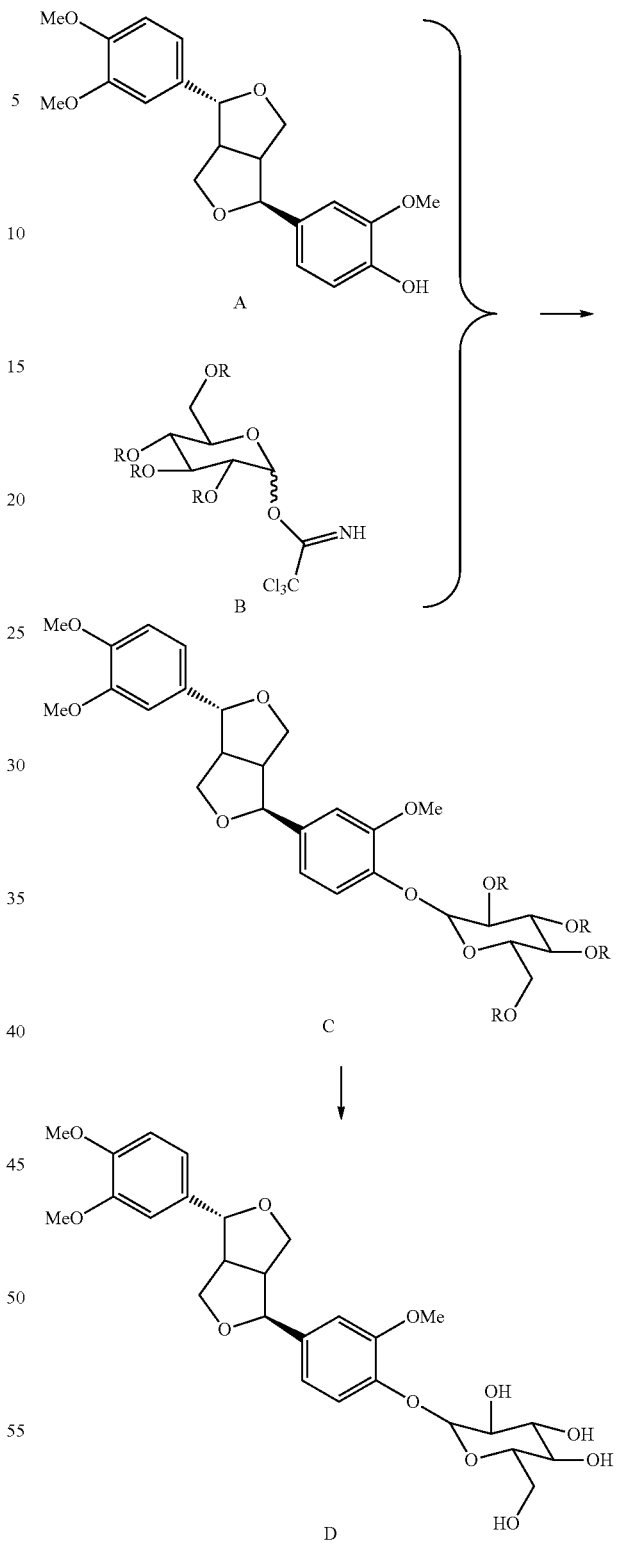

wherein the structural Formula A is phillygenin; structural Formula B is 2,3,4,6-tetra-O-acyl-D-glucopyranosyl trichloroacetimidate; structural Formula C is tetra-acylphillyrin; structural Formula D is phillyrin.

The advantages and practical values of the chemical synthesis method for phillyrin of the invention lie in: the raw material is easy to get, the catalysts for glycosylation are cheap and easy to get, the production cost is greatly reduced, and it can be used for industrial production.

DETAILED DESCRIPTION OF THE INVENTION

The invention will be further described by the following examples, however, these examples are merely illustrative of the present invention and not be construed as any limits to the scope of the present invention. Further, the reagents and raw materials in the examples may be obtained commercially, if there are omissions, organic synthesis guidelines, guidelines from drug administrations and instructions from the corresponding apparatuse and reagent manufacturers can be referred to.

Embodiment 1

1) Glycosylation

Phillygenin (372 mg, 0.001 mol) and 2,3,4,6-tetra-O-acetyl-D-glucopyranosyl trichloroacetimidate (738 mg, 0.0015 mol) are fed into a three-necked flask of 100 mL, in which the molar ratio of phillygenin to 2,3,4,6-tetra-O-acetyl-D-glucopyranosyl trichloroacetimidate is 1:1.5, 20 mL of anhydrous dichloromethane and a 4 Å-type aluminosilicate molecular sieve (744 mg) are added to the flask; then inert gas nitrogen is introduced into the flask for inert gas protection, followed by stirring for 0.5 h, after evenly mixing, trimethylsily ltriflate as Lewis acid catalyst (TMSOTf, 0.06 mL, 0.312 mmol) is added dropwise, in which the molar ratio of Lewis acid catalyst to 2,3,4,6-tetra-O-acetyl-D-glucopyranosyl trichloroacetimidate is 1:5, the mass ratio of molecular sieve to phillygenin is 2:1, the resulting mixture is subjected to glycosylation for 10 h at 0° C. under stirring;

the reactive intermediate obtained from dehydrogenation of hydroxy groups of a reaction substrate phillygenin with Lewis acid may be oxidized when being exposed to oxygen, the possibility of the intermediate being exposed to oxygen is eliminated by inert gas protection to ensure the normal reaction; since glycosylation may produce water, the molecular sieve is added for the purpose of removing the resulting water from reaction to ensure the normal reaction, meanwhile TMSOTf may be decomposed by water, the molecular sieve is added to further ensure the normal reaction.

2) Quenching Treatment

Triethylamine as quenching agent (0.312 mmol) is added to the reaction mixture to quench glycosylation, in which the molar ratio of triethylamine as quenching agent to trimethylsilyl trifluoromethanesulphonate (i.e trimethylsilyl triflate) as Lewis acid catalyst is 1:1; then the quenched glycosylation mixture is filtered using a buchuer funnel, the filtrate is concentrated and purified by silica gel column chromatography (eluent: petroleum ether/ethyl acetate=3:2 (v/v)), to obtain tetraacetyl phillyrin;

3) Deacylation Treatment 3-1) tetraacetyl phillyrin is dissolved in 30 ml of a mixture of dichloromethane and methanol, in which the volume ratio of dichloromethane to methanol is 1:2, then sodium methoxide (0.22 mg, 0.004 mmol) is added, in which the molar ratio of sodium methoxide to 2,3,4,6-tetra-O-acetyl-D-glucopyranosyl trichloroacetimidate is 1:375, followed by deacylation reaction for 4 h under stirring, then acetic acid as pH adjustor is added to adjust the pH value of the resulting mixture from deacylation reaction to 6;

During the deacylation reaction of the present invention, sodium methoxide added does not cause alkalinity-induced destruction of glycosidic bonds and also serves as a base for deacylation reaction to remove acyl-protecting groups and thus to promote the proceed of glycosylation. The time of deacylation reaction is at least 4 h, preferably 4-12 h.

In the invention, acetic acid is added to the deacylated mixture to adjust pH of the mixture and neutralize excessive sodium methoxide, terminating the reaction, further, owing to moderate activity, acetic acid does not break the generated glycosidic bonds and could increase the yield of product.

3-2) the resulting mixture is concentrated under vacuum with a rotary evaporator to remove the solvents by evaporation, followed by purification through silica gel column chromatography (eluent: chloroform/methanol=8:2 (v/v)), 400.5 mg white solid phillyrin is obtained with a total yield of 79.8%.

The white solid has a melting point of 181-183° C. and is soluble in chloroform and methanol. It has the same physical property as the phillyrin standard substance (purchased from The National Institute For Food and Drug Control), keeps melting point unchanged after being mixed with the phillyrin standard substance, and has a spectral and a mass spectrometric data which are consistent with those of phillyrin reported in study papers, thus this compound is identified as phillyrin.

In accordance with HPLC listed in Appendix VI D to First Volume of Chinese Pharmacopoeia (ChP, 2000), the purity of the prepared phillyrin is 99.5%.

ESI-MS, m/z [M-H] is 533, the molecular weight is 534.

$^1$HNMR (600 MHz, d6-DMSO) δ: 7.66 (br, 1H, OH), 7.49 (d, 1H, J=8.43 Hz), 7.21 (br, 2H), 7.14 (s, 1H), 7.13 (s, 1H), 7.01 (d, 1H. J=7.89 Hz), 6.92 (d, 1H, J=8.12 Hz), 6.88 (d, 1H, J=8.34 Hz), 6.54 (br, 1H), 5.60 (d, 1H, J=7.03 Hz), 4.82 (d, 1H, J=5.92 Hz), 4.54 (d, 1H, J=6.78 Hz), 4.42 (d, 1H, J=11.43 Hz), 4.25 (m, 4H), 4.13 (d, 1H, J=9.18 Hz), 4.01 (br, 1H), 3.90 (t, 1H, J=8.72 Hz), 3.75 (dd, 1H, J=8.99 Hz, 6.43 Hz), 3.68 (s, 3H), 3.65 (s, 3H), 3.64 (s, 3H), 3.44 (t, 1H, J=8.72 Hz), 3.27 (m, 1H), 2.82 (q, 1H, J=6.78 Hz).

$^{13}$CNMR (150 MHz, d6-DMSO) δ: 50.65 (C-9), 55.33 (C-31), 56.04 (C-32), 56.09 (C-8), 56.12 (C-11), 62.50 C-29), 70.20 (C-12), 71.38 (C-34), 71.43 (C-13), 75.03 (C-33), 78.69 (C-10), 79.04 (C-30), 82.43 (C-2), 88.07 (C-21), 102.53 (C-25), 110.52 (C-6), 111.20 (C-3), 112.47 (C-5), 116.37 (C-27), 118.58 (C-4), 119.22 (C-23), 132.29 (C-17), 136.40 (C-20), 147.60 (C-36), 149.09 (C-38), 150.35 (C-28), 150.38 (C-24).

Embodiment 2

1) Glycosylation

Phillygenin (372 mg, 0.001 mol) and 2,3,4,6-tetra-O-benzoyl-D-glucopyranosyl trichloroacetimidate (1.11 g, 0.0015 mol) are fed into a three-necked flask of 100 mL, in which the molar ratio of phillygenin to 2,3,4,6-tetra-O-benzoyl-D-glucopyranosyl trichloroacetimidate is 1:1.5, 20 mL of anhydrous dichloromethane and a 3 Å-type aluminosilicate molecular sieve (744 mg) are added, then inert gas argon is introduced for inert gas protection, followed by stirring for 0.5 h, 80 mg (0.312 mmol) silver trifluoromethanesulfonate as Lewis acid catalyst is added dropwise, in which the molar ratio of Lewis acid catalyst to 2,3,4,6-tetra-O-benzoyl-D-glucopyranosyl trichloroacetimidate is 1:5, the mass ratio of molecular sieve to phillygenin is 2:1, the resulting mixture is subjected to glycosylation for 8 h at 10° C. under stirring;

the molecular sieve is added for the purpose of removing the resulting water from reaction to ensure the positive proceed of reaction.

2) Quenching Treatment

Sodium thiosulfate as quenching agent (0.312 mmol) is added to the reaction mixture to quench glycosylation, in which the molar ratio of sodium thiosulfate as quenching agent to trimethylsilyl trifluoromethanesulphonate as Lewis acid catalyst is 1:1; then the quenched glycosylation mixture is filtered using a buchuer funnel, the filtrate is concentrated and purified by silica gel column chromatography (eluent: petroleum ether/ethyl acetate=2:1 (v/v)), to obtain tetra-benzoyl-phillyrin;

3) Deacylation Treatment 3-1) tetra-benzoyl-phillyrin is dissolved in 30 ml of a mixture of dichloromethane and methanol, in which the volume ratio of dichloromethane to methanol is 1:2, then sodium methoxide (0.22 mg, 0.004 mmol) is added, in which the molar ratio of sodium methoxide to 2,3,4,6-tetra-O-benzoyl-D-glucopyranosyl trichloroacetimidate is 1:375, followed by deacylation reaction for 4 h under stirring, then acetic acid as pH adjustor is added to adjust the pH value of the resulting mixture from deacylation reaction to 7;

3-2) the resulting mixture is concentrated under vacuum with a rotary evaporator to remove the solvents by evaporation, followed by purification through silica gel column chromatography (eluent: chloroform/methanol=8:2 (v/v)), 373.8 mg white solid phillyrin is obtained with a total yield of 70%.

The physicochemical properties, spectral data and mass spectrometric data of the purified white solid product are consistent with those of phillyrin reported in study papers, thus this compound is identified as phillyrin.

Embodiment 3

1) Glycosylation

Phillygenin (372 mg, 0.001 mol) and 2,3,4,6-tetra-O-acetyl-D-glucopyranosyl trichloroacetimidate (1.23 g, 0.0025 mol) are fed into a three-necked flask of 100 mL, in which the molar ratio of phillygenin to 2,3,4,6-tetra-O-acetyl-D-glucopyranosyl trichloroacetimidate is 1:2.5, 20 mL of anhydrous dichloromethane and a 5 Å-type aluminosilicate molecular sieve (744 mg) are added, then inert gas nitrogen is introduced for inert gas protection, followed by stirring for 0.5 h, trimethylsilyltriflate as Lewis acid catalyst (0.08 mL, 0.416 mmol) is added dropwise, in which the molar ratio of Lewis acid catalyst to 2,3,4,6-tetra-O-acetyl-D-glucopyranosyl trichloroacetimidate is 1:6, the mass ratio of molecular sieve to phillygenin is 2:1, the resulting mixture is subjected to glycosylation for 10 h at 0° C. under stirring;

2) Quenching Treatment

Triethylamine as quenching agent (0.416 mmol) is added to the reaction mixture to quench glycosylation, in which the molar ratio of triethylamine as quenching agent to trimethylsilyl trifluoromethanesulphonate as Lewis acid catalyst is 1:1; then the quenched glycosylation mixture is filtered using a buchuer funnel, the filtrate is concentrated and purified by silica gel column chromatography (eluent: petroleum ether/ethyl acetate=3:2 (v/v)), to obtain tetra-acetyl phillyrin;

3) Deacylation Treatment 3-1) tetra-acetyl phillyrin is dissolved in 30 ml of a mixture of dichloromethane and methanol, in which the volume ratio of dichloromethane to methanol is 1:2, then sodium methoxide (0.337 mg, 0.00625 mmol) is added, in which the molar ratio of sodium methoxide to 2,3,4,6-tetra-O-acetyl-D-glucopyranosyl trichloroacetimidate is 1:400, followed by deacylation reaction for 4 h under stirring, then acetic acid as pH adjustor is added to adjust the pH value of the resulting mixture from deacylation reaction to 6;

3-2) the resulting mixture is concentrated under vacuum with a rotary evaporator to remove the solvents by evaporation, followed by purification through silica gel column chromatography (eluent: chloroform/methanol=8:2 (v/v)), to obtain 384.4 mg white solid phillyrin, with a total yield of 72%.

The physicochemical properties, spectral data and mass spectrometric data of the purified white solid product are consistent with those of phillyrin reported in study papers, thus this compound is identified as phillyrin.

Embodiment 4

1) Glycosylation

Phillygenin (372 mg, 0.001 mol) and 2,3,4,6-tetra-O-acetyl-glucopyranosyl trichloroacetimidate (492.6 mg, 0.001 mol) are fed into a three-necked flask of 100 mL, in which the molar ratio of phillygenin to 2,3,4,6-tetra-O-acetyl-glucopyranosyl trichloroacetimidate is 1:1, 20 mL of anhydrous dichloromethane and a 4 Å-type aluminosilicate molecular sieve (744 mg) are added to the flask; then inert gas nitrogen is introduced for inert gas protection, followed by stirring for 0.5 h, boron trifluoride-ethyl ether complex as Lewis acid catalyst (0.025 mL, 0.2 mmol) is added dropwise, in which the molar ratio of Lewis acid catalyst to 2,3,4,6-tetra-O-acetyl-glucopyranosyl trichloroacetimidate is 1:5, the mass ratio of molecular sieve to phillygenin is 2:1, the resulting mixture is subjected to glycosylation for 10 h at 0° C. under stirring;

2) Quenching Treatment

Triethylamine as quenching agent (0.2 mmol) is added to the reaction mixture to quench glycosylation, in which the molar ratio of triethylamine as quenching agent to boron trifluoride etherate as Lewis acid catalyst is 1:1; then the quenched glycosylation mixture is filtered using a buchuer funnel, the filtrate is concentrated and purified by silica gel column chromatography (eluent: petroleum ether/ethyl acetate=3:2 (v/v)), to obtain tetra-acetyl phillyrin;

3) Deacylation Treatment 3-1) tetraacetyl phillyrin is dissolved in 30 ml of a mixture of dichloromethane and methanol, in which the volume ratio of dichloromethane to methanol is 1:2, then sodium methoxide (0.11 mg, 0.002 mmol) is added, in which the molar ratio of sodium methoxide to 2,3,4,6-tetra-O-acetyl-D-glucopyranosyl trichloroacetimidate is 1:500, followed by deacylation reaction for 12 h under stirring, then acetic acid as pH adjustor is added to adjust the pH value of the resulting mixture from deacylation reaction to 7;

3-2) the resulting mixture is concentrated under vacuum with a rotary evaporator to remove the solvents by evaporation, followed by purification through silica gel column chromatography (eluent: chloroform/methanol=8:2 (v/v)), to obtain 400.5 mg white solid phillyrin, with a total yield of 75%.

The physicochemical properties, spectral data and mass spectrometric data of the purified white solid product are consistent with those of phillyrin reported in study papers, thus this compound is identified as phillyrin.

Test Example: Antiviral Test of Phillyrin

1 Antiviral Test In Vitro 1.1 Test Materials (1) Drugs: the following drugs were dissolved with purified water, filtered, sterilized, divided and stored at 4° C. until use.

1) Phillyrin: white solid, available from Dalian Fusheng Natural Drug Development Co., Ltd. Purity: 99.1%, determined by HPLC equipped with both UV detector and evaporative light-scattering detector (ELSD) using area normalization method;

2) Ribavirin injection: a colorless transparent liquid produced by Henan Runhong Pharmaceutical Co., Ltd., with Batch No.: 1206261; National medical Permittent No.: H19993553; used as the positive control drug at 100 mg/ml in this test;

3) Oseltamivir phosphate, available from National Institute for Control of Pharmaceutical & Biological Products, with Batch No. 101096-200901;
used as the positive control drug at 100 mg/injection in this test.

(2) Cell Strain

Vero Cell strain (African green monkey kidney cells) is preserved by College of Basic Medical Sciences of Jilin University.

(3) Virus Strains

1) Influenza virus, parainfluenza virus and respiratory syncytical virus (RSV) were all commercially available from the Virus Institute of Chinese Preventive Medicine Academy of Science;

2) Coxsackie virus B3 (CVB3) strain was available from USA and preserved by our teaching and research office;

3) Coxsackie virus A16 (CoxA16) strain and enterovirus EV71 strain were donated by Sendai National Hospital in Japan and preserved by our teaching and research office.

4) Adenovirus (AdV) strain was available from the Pediatric Research department of The First Hospital of Norman Bethune Medical University.

5) Herpes simplex virus type I (HSV-1) was purchased from The Institute for the Control of Pharmaceutical and Biological Products, Ministry of Health.

(4) Main Instruments and Reagents

| Biological safety cabinet | BHC-1300 II A/B3, AIRTECH |
|---|---|
| $CO_2$ Incubator | MCO-18AIC, SANYO |
| Inverted microscope | CKX41, OLYMPUS |
| Electronic analytical balance | AR1140/C, DHAUS |
| Culture medium | DMEM, HyClone |
| Fetal bovine serum | HyClone |
| Trypsin | Gibco |
| MTT | Sigma |

DMSO was available from Tianjin Beilian Fine Chemicals Development Co., Ltd.

1.2 Test Methods (1) Cell Preparation

Vero cells were subcultured for 1-2 days to form a film. Cultures were then submitted to trypsin digestion after exhibiting clearly observable boundaries and strong tri-dimensional sense and diopter. The digestion was drained after needle-like holes occurred on the cell surface, then cells were dispersed with a few milliliters of medium, counted, then diluted to about $5 \times 10^7$ cells/L with DMEM containing 10% fetal bovine serum and transferred to a 96-pore culture plate until monolayer formed.

(2) Drug Toxicity Assay

Cytotoxicity test: the drugs were diluted according to the concentrations shown in Table 1-1 for cytotoxicity assays.

TABLE 1-1

Reference table for diluting drugs (unit: g/L)

| Drug | concentration gradient | | | | | | | |
|---|---|---|---|---|---|---|---|---|
| | Gradient 1 | Gradient 2 | Gradient 3 | Gradient 4 | Gradient 5 | Gradient 6 | Gradient 7 | Gradient 8 |
| Phillyrin | 5 | 2.5 | 1.25 | 0.625 | 0.3125 | 0.15625 | 0.078125 | 0.039063 |
| Ribavirin | 5 | 2.5 | 1.25 | 0.625 | 0.3125 | 0.15625 | 0.078125 | 0.039063 |
| Oseltamivir phosphate | 2 | 1 | 0.5 | 0.25 | 0.125 | 0.0625 | 0.03125 | 0.015625 |

Different concentrations of drugs diluted with the above maintenance medium (DMEM containing 2% fetal calf serum) were added dropwise to Vero monolayer cells with 0.2 ml per pore, and for each concentration, the drugs were added in sextuplicate in 6 pores respectively. In addition, 6 pores were set up as normal control (without drugs) while another 6 pores as blank control (medium only). Cells were grown in a 37° C. incubator under 5% $CO_2$. CPE was visualized under the invert microscope and recorded daily. After 72 h, 20 μL MTT solution (5 mg·mL$^{-1}$) was added into each pore and incubated for 4 h. The culture medium in each pore was sucked and discarded, 100 μL DMSO was added to each pore. Then the culture was shaken for 5 min, measured OD value at 492 nm to calculate the cell survival ratio. The cell survival ratio was analyzed using a Probit regression model in SPSS 18.0 statistical software, and the maximal nontoxic concentration ($TC_0$) and median toxic concentration ($TC_{50}$) of drugs against Vero cells were calculated.

(3) Determination of TCID50 for Each Virus

A 10-fold serial dilution was performed on each virus to give $10^{-1}$, $10^{-2}$, $10^{-3}$, $10^{-4}$, $10^{-5}$ and $10^{-6}$ dilutions. To each of sextuplicate pores of a 96-pore culture plate containing monolayer Vero cells was inoculated 100 μl diluent for each dilution in-sequence while the normal cell control was set up. The plates were incubated for 2 h at 37° C. in 5% $CO_2$ followed by the removal of virus solution, and 100 μL cell maintenance medium was added to each pore for further incubation at 37° C. in 5% $CO_2$. The cytopathic effect was examined under the microscope from the $3^{rd}$ day on, and the results were determined and recorded on the $7^{th}$-$8^{th}$ day. The virus titer was calculated by karber method with maximal dilution titer that allowed positive cytopathy to occur in 50% of the cell pores as the end point.

$$\text{Equation } Log TCID_{50} = XM + \frac{1}{2}d - d\frac{\Sigma Pi}{100}$$

$TCID_{50}$: 50% histocyte infection dose

XM: logarithm of the highest concentration dilution of virus d: logarithm of dilution coefficient (multiple)

Σpi: the sum of the cytopathy percentages for each dilution (4) Impact of the Drugs on the Virus-Induced Cytopathy The culture medium in plates covered with monolayer cells was aspirated and attacking viruses at a dose of 100 $TCID_{50}$ were inoculated into the cells for subsequent attachment in 37° C. incubator under 5% $CO_2$ for 2 h, and then added of certain concentration (maximal non-cytotoxic concentration or so) of each medical fluid. Each concentration was performed in sextuplicate in 6 pores with 200 μL/pore. Ribavirin injection and oseltamivir phosphate served as positive control groups while normal control group (without virus and drug) and virus control group (adding virus but no drug) were set up to examine the effect of drugs on virus-induced CPE. After 72 h, the OD value is measured under 492 nm wavelength by using an MTT colorimetric method, and the antiviral effective rate (ER %) of the drug was calculated. The analysis of variance (ANOVA) method in SPSS 18.0 statistical software was used to determine if there was a significant difference among different drugs groups on antiviral efficiency.

ER %=(mean OD value of drug-treated groups–mean OD value of virus control groups)/(mean OD value of cell control groups–mean OD value of virus control groups)×100%

1.3 Results (1) $TCID_{50}$ for Each Virus $Log TCID_{50} = -2 + 0.5 - \frac{100+100+50}{100} = -4$  Parainfluenza virus $Log TCID_{50} = -2 + 0.5 - \frac{100+100+50}{100} = -4$  Influenza virus $Log TCID_{50} = -2 + 0.5 - \frac{100+100+100+50}{100} = -5$  $CVB_3$ $Log TCID_{50} = -2 + 0.5 - \frac{100+100+100+30}{100} = -4.8$  HSV-1

$Log TCID_{50} = -2 + 0.5 - \frac{100+100+50}{100} = -4$  AdV $Log TCID_{50} = -2 + 0.5 - \frac{100+100+100+50}{100} = -5$  RSV $Log TCID_{50} = -2 + 0.5 - \frac{100+100+100+50}{100} = -5$  CoxA16

$Log TCID_{50} = -2 + 0.5 - \frac{100+100+100+50}{100} = -5$  EV71

(2) Drug Toxicity Determination

1) Determination of Cytotoxicity of Drugs

The maximal non-cytotoxic concentration ($TC_0$), median toxic concentration ($TC_{50}$) of each drug against Vero cells, and the concentrations of drugs used in antiviral assay were shown in table 1-2.

TABLE 1-2

Results of drug cytotoxicity assay (unit: g/L)

| Viruses | Drugs | | |
| --- | --- | --- | --- |
|  | Phillyrin | Ribavirin | Oseltamivir phosphate |
| Maximal non-cytotoxic concentration | 0.006 | 0.065 | 0.28 |
| Median toxic concentration | 0.55 | 1.392 | 0.832 |
|  | 0.30 | 0.01 | 0.70 | 0.30 |

2) Results of Protective Effects of the Drugs on the Virus-Induced Cytopathy

Results of antiviral efficiencies of drugs and one-way analysis of variance (ANOVA) were shown in table 1-3.

TABLE 1-3

Statistical table for antiviral efficiencies of drugs (ER %)

| Viruses | Drugs | | |
| --- | --- | --- | --- |
|  | Phillyrin | Ribavirin | Oseltamivir phosphate |
| Influenza virus | 75.38** | 57.49** | 81.76** |
| Parainfluenza virus | 84.96** | 91.56** | 94.52** |
| CoxA16 | 75.08** | 0.70 | 2.95 |
| RSV | 80.40** | 50.08* | 37.60 |
| HSV-I | 85.00** | 62.92** | 66.56** |
| ADV | 75.14** | 0.43 | 10.31 |
| EV71 | 84.85** | 4.25 | 51.86 |
| $CVB_3$ | 75.27** | 13.44 | 1.64 |

The results in table 1-3 showed that inhibitory effects of phillyrin on influenza virus, parainfluenza virus, respiratory syncytical virus (RSV), coxsackie virus $B_3(CVB_3)$, coxsackie virus A16 (CoxA16), enterovirus EV71, adenovirus (AdV) and herpes simplex virus type I (HSV-1) were significant; Wherein, the inhibitory effects on influenza virus, parainfluenza virus and herpes simplex virus type I (HSV-1) were comparable to the antiviral effects of positive drugs such as ribavirin and oseltamivir phosphate (Tamiflu); and the inhibitory effects on coxsackie virus B3 (CVB3), coxsackie virus A16 (CoxA16), enterovirus EV71 and adenovirus (AdV) were more remarkable than that of positive drugs such as ribavirin and oseltamivir phosphate (Tamiflu).

2. Antiviral Test In Vivo

2.1 Experimental Materials (1) Experimental Animals

Kunming mice were provided by Experimental Animal Center of Norman Bethune Health Science Center of Jilin University. Medicinal animal No. 10-5219

(2) Experimental Instruments

Quantitative PCR Instrument: 7300, ABI;

PCR Instrument: ES-60J, Shenyang Longteng Electronic Weighing Instrument Co., Ltd.;

Electronic analytical balance: FA1004, Shenyang Longteng Co., Ltd.

CO2 Incubator: HG303-5, Nanjing Experimental Instrument Factory;

Superclean bench: SW-CJ-IF, Suzhou Antai Air Tech Co., Ltd.;

Invert microscope: CKX41, Olympus Instrument;

−80° C. ultra-low temperature freezer: TECON-5082, Australia;

Water bath oscillator: HZS-H, Harbin Donglian Electronic technology Development Co., Ltd.;

Microplate reader: TECAN A-5082, Australia;

Spectrophotometer: model 7550; Japan.

2.2 Experimental Methods (1) Study on the Effect of Phillyrin on Pneumonia Induced by Influenza Virus and Parainfluenza Virus Infection 1) Experimental Animal and Group Division 140 four weeks-old Kunming mice were adopted to perform two tests. 140 mice were adopted and randomly divided into 14 groups (n=10 in each group) for the determination of the lung index and the inhibitory rate of the lung index after administration of phillyrin to mice infected with influenza virus and parainfluenza virus.

2) Infection Method

A plug of absorbent cotton was placed into the beaker (200~300 ml) and an appropriate amount of ethyl ether was poured thereto until the absorbent cotton became wet. The beaker supplied with the absorbent cotton was inverted upside down before the mouse was placed thereto for anesthesia. After the mice experienced extreme excitement and obvious weakness, they were placed in a supine position and infected nasally with 15LD50 influenza virus and parainfluenza virus at 0.03 ml/nostril. In normal control group, virus suspension was replaced with normal saline.

3) Administration Method and Administration Doses

Each mice were administered intragastrically with phillyrin, ribavirin and oseltamivir phosphate the day before infection. Phillyrin was administered in a high dosage of 13 mg/kg, in a medium dosage of 6.5 mg/kg or in a low dosage of 3.25 mg/kg while the dosages of positive drugs ribavirin and oseltamivir phosphate were 19.5 mg/kg and 58.5 mg/kg, respectively. The administration can be performed once per day for five consecutive days. The virus control group was drenched with normal normal saline of the same volume.

4) Lung Index Determination

In the fifth day after drugs are administered by mice, access to water was prevented and after 8 h, the mice were weighed and then sacrificed by exsanguination through eye enucleation. Then the lungs were removed after the opening of the chest, washed twice with normal saline followed by removal of the moisture from surface with a filter paper and weighed. Lung index and the inhibitory rate of the lung index were calculated according to the following equations:

Lung index=Mouse lung weight/Mouse body weight×100%

Inhibitory rate of the lung index=(Mean lung index of the infection model group−Mean lung index of the experimental group)/Mean lung index of the infection model group×100%

2.3 Experimental Results and Analysis

After mice were infected with influenza virus and parainfluenza virus, the mean results of lung index showed that phillyrin ranging from 3.25 to 13.0 mg/kg/d provided substantial protection to mice lung tissue under the infection of influenza virus and parainfluenza virus, with the lung indexes of both significantly reduced. Results were shown in Tables 2-1 and 2-2.

TABLE 2-1

Lung indexes and inhibitory rates of the lung index of mice administrated with phillyrin after influenza virus infection (n = 3)

| Groups | Drug doses (mg/kg/d) | Lung index ($\bar{X} \pm S$) | Lung index Inhibitory rate (%) | P value |
|---|---|---|---|---|
| Normal control group | 0 | 1.277 ± 0.105 | — | |
| Virus control group | 0 | 1.502 ± 0.088 | — | |
| Ribavirin group | 58.5 | 1.303 ± 0.060 | 13.24 | *<0.05 |
| Oseltamivir phosphate group | 19.5 | 1.191 ± 0.062 | 20.71 | **<0.01 |
| Phillyrin high-dose group | 13.0 | 1.290 ± 0.041 | 14.51 | **<0.01 |
| Phillyrin medium-dose group | 6.5 | 1.307 ± 0.068 | 12.97 | *<0.05 |
| Phillyrin low-dose group | 3.25 | 1.339 ± 0.045 | 10.82 | *<0.05 |

Compared with virus control group: *P < 0.05, **P < 0.01.

TABLE 2-2

Lung indexes and inhibitory rates of the lung index of mice administrated with phillyrin after parainfluenza virus infection (n = 3)

| Groups | Drug doses (mg/kg/d) | Lung index ($\bar{X} \pm S$) | Lung index Inhibitory rate (%) | P value |
|---|---|---|---|---|
| Normal control group | 0 | 1.316 ± 0.031 | — | |
| Virus control group | 0 | 1.601 ± 0.071 | — | |
| Ribavirin group | 58.5 | 1.358 ± 0.065 | 15.19 | *<0.05 |
| Oseltamivir phosphate group | 19.5 | 1.256 ± 0.057 | 21.56 | *<0.05 |
| Phillyrin high-dose group | 13.0 | 1.2297 ± 0.071 | 19.01 | *<0.05 |
| Phillyrin medium-dose group | 6.5 | 1.327 ± 0.064 | 17.11 | *<0.05 |
| Phillyrin low-dose group | 3.25 | 1.360 ± 0.052 | 15.03 | *<0.05 |

Compared with virus control group: *P < 0.05.

2.4 Conclusion

The results of the antiviral test in vivo showed that phillyrin dosage ranging from 3.25 to 13.0 mg/kg/d had a significant inhibitory effect on mice viral pneumonia induced by influenza virus and parainfluenza virus and could greatly reduce both of their lung indexes and hemagglutination titers, and represented a significant difference compared to virus control group.

The invention claimed is:

1. A chemical synthesis method for phillyrin, which comprises the following steps:
    1) dissolving the glycosyl receptor phillygenin and the glycosyl donor 2,3,4,6-tetra-O-acyl-D-glucopyranosyl trichloroacetimidate in a first organic solvent for glycosylation in the presence of a catalyst and a molecular sieve under protection of an inert gas to obtain tetraacyl phillyrin, wherein the catalyst is a Lewis acid, the molecular sieve is an aluminosilicate molecular sieve or aluminosilicate powder, and the first organic solvent is dichloromethane, trichloromethane, 1,2-dichloroethane or toluene;
    2) dissolving the tetraacyl phillyrin in a second organic solvent, adding sodium methoxide for deacylation, adding an acidic pH regulator to regulate pH value of the reaction mixture to neutral, and carrying out purification treatment to obtain phillyrin, wherein the second organic solvent is a mixed solution of dichloromethane and methanol.

2. The method according to claim 1, characterized in that a molar ratio of the catalyst to the glycosyl donor 2,3,4,6-tetra-O-acyl-D-glucopyranosyl trichloroacetimidate is 1:1-10.

3. The method according to claim 1, which comprises the following steps:
    1) dissolving the glycosyl receptor phillygenin and the glycosyl donor 2,3,4,6-tetra-O-acyl-D-glucopyranosyl trichloroacetimidate in a first organic solvent for glycosylation in the presence of a catalyst and a molecular sieve under protection of an inert gas to obtain tetraacyl phillyrin, wherein the catalyst is a Lewis acid, the molecular sieve is an aluminosilicate molecular sieve or aluminosilicate powder, and the first organic solvent is dichloromethane, trichloromethane, 1,2-dichloroethane or toluene;
    1A) adding a quenching agent to the reaction mixture obtained in step 1) to quench the glycosylation reaction;
    2) dissolving the tetraacyl phillyrin in a second organic solvent, adding sodium methoxide for deacylation, adding an acidic pH regulator to regulate pH value of a reaction mixture to neutral, and carrying out purification treatment to obtain phillyrin, wherein the second organic solvent is a mixed solution of dichloromethane and methanol.

4. The method according to claim 1, comprising step 1A) of adding a quenching agent to the reaction mixture obtained by step 1) to quench the glycosylation reaction.

5. The method according to claim 1, characterized in that in step 2), a molar ratio of sodium methoxide to 2,3,4,6-tetra-O-acyl-D-glucopyranosyl trichloroacetimidate is 1:300-500.

6. The method according to claim 1, characterized in that a volume ratio of dichloromethane to methanol in the mixed solution of dichloromethane and methanol is 1:1-10.

* * * * *